United States Patent [19]
DeLuca et al.

[11] 4,448,726
[45] May 15, 1984

[54] RING A- AND TRIENE-MODIFIED VITAMIN D COMPOUNDS

[75] Inventors: Hector F. DeLuca; Heinrich K. Schnoes, both of Madison; Herbert E. Paaren, Deerfield; Connie M. Smith, Madison, all of Wis.

[73] Assignee: Wisconsin Alumni Research Foundation, Madison, Wis.

[21] Appl. No.: 493,537

[22] Filed: May 11, 1983

[51] Int. Cl.$^3$ .............................................. C07J 9/00
[52] U.S. Cl. .................................................. 260/397.2
[58] Field of Search ..................................... 260/397.2

[56] References Cited

U.S. PATENT DOCUMENTS 4,229,359 10/1980 DeLuca et al. ................ 260/397.2
4,358,406 11/1982 DeLuca et al. ................ 260/397.2
4,360,472 11/1982 DeLuca et al. ................ 260/397.2

Primary Examiner—Elbert L. Roberts
Attorney, Agent, or Firm—Howard W. Bremer

[57] ABSTRACT

This invention is directed to a new class of vitamin D compounds which are characterized by a modified ring A and triene structures and to a method for preparing same. The 7,8-dihydroxy-, 10.19-dihydroxy- and 10-oxo-19-nor-analogs of 25-hydroxyvitamin $D_3$ are specifically disclosed.

9 Claims, No Drawings

RING A- AND TRIENE-MODIFIED VITAMIN D COMPOUNDS

This invention relates to the preparation of vitamin D compounds in which ring A and/or the triene chromophore is modified.

The discovery of biologically active vitamin D metabolites, characterized by hydroxy substitution at carbon 1 and/or carbon 25 of the vitamin D skeleton has led to much activity in the area of the chemical synthesis of vitamin D compounds. Much of that activity has been concerned with the preparation of the biological metabolites and of close structural analogs of these compounds. Synthetic approaches and results are summarized in a number of recent reviews (e.g. DeLuca et al., Topics in Current Chemistry, vol. 83, p. 1 (1979); Yakhimovich, Russian Chem. Revs. 49, 371 (1980); Lythgoe, Chem. Soc. Rev. 9, 449 (1980).

The present invention relates to the preparation of a new class of vitamin D compounds characterized by modified ring A and triene structures. More specifically, the invention concerns 7,8-dihydroxy-, 10,19-dihydroxy- and the 10-oxo-19-nor-analogs of 25-hydroxyvitamin $D_3$ (25-hydroxycholecalciferol) and the hydroxy-protected derivatives thereof.

The term 'hydroxy-protecting group', as used in this specification or the claims, means any of the conventional protecting groups such as acyl, alkylsilyl, tetrahydropyranyl, methoxymethyl. The term 'acyl' signifies an aliphatic acyl group, of from 1 to 5 carbons, in all its isomeric forms, or an aromatic acyl group, such as benzoyl, or halogen-, alkyl- or nitro-substituted benzoyl radicals. The term 'alkyl' refers to an aliphatic hydrocarbon radical of 1 to 5 carbons in all its isomeric forms, e.g. methyl, ethyl, propyl, tert.-butyl, etc.

The novel compounds of this invention can be prepared as follows:

Treatment of a 3,5-cyclovitamin derivative of 25-hydroxyvitamin $D_3$, (e.g. 25-hydroxy-3,5-cyclovitamin $D_3$ 6-methyl ether, a known compound, prepared from 25-hydroxycholecalciferol, by the method of DeLuca et al., U.S. Pat. No. 4,195,027) with osmium tetroxide in pyridine solution gives the corresponding 10,19-dihydroxy analog, represented by structure 1 below, where $R_1$, $R_2$ and $R_3$ represent hydrogen and X is an alkyl group, e.g. methyl.

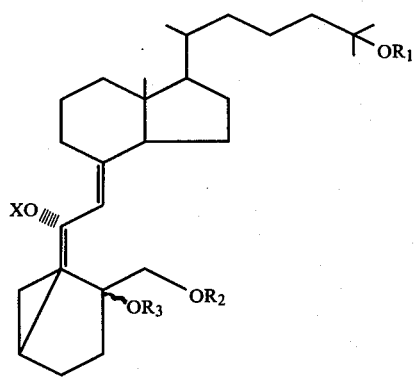

1

-continued

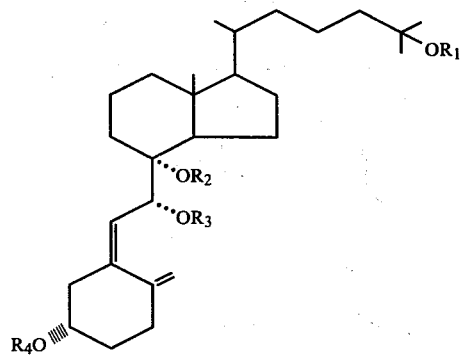

2

The regiospecifity of this reaction, i.e. the specific hydroxylation of the 10(19)-double bond, in preference to the alternative 7,8-double bond, is remarkable and unexpected, especially so, since treatment of 25-hydroxycholecalciferol 3-acylate itself, with osmium tetroxide under similar conditions leads to the 7,8-dihydroxy analog, structure 2 above ($R_1$, $R_2$, $R_3$=H and $R_4$=Acyl) where again the absence of hydroxylation at any of the other available double bonds (C-5,6 and C-10(19)) is a very notable feature. Both compounds 1 and 2 above are novel products. A 7,8-dihydroxy vitamin $D_2$ compound is known (see Lythgoe, supra). Using the above general procedure, the osmomylation of other 25-hydroxy-cyclovitamin D analogs, e.g. the known 25-hydroxy-3,5-cyclovitamin $D_3$ 6-alkyl ethers, where the alkyl group is, for example, ethyl, propyl, isopropyl, butyl, etc., provides the corresponding 10,19-dihydroxy compounds of general structure 1, above, where $R_1$, $R_2$ and $R_3$ represent hydrogen and X is an alkyl group as present in the starting material, e.g. ethyl, propyl, isopropyl, butyl, etc., and these 6-O-alkyl analogs are also suitable substrates for the subsequent reaction processes described herein.

From the hydroxy compounds thus prepared, the corresponding hydroxy-protected derivatives are obtained by conventional hydroxy-protecting procedures known in the art (e.g. conventional acylation or alkylsilylation procedures) to obtain the corresponding partially or fully hydroxy-protected derivatives represented by structures 1 or 2 above, where any or all of $R_1$, $R_2$, $R_3$ and $R_4$, represent hydroxy-protecting groups.

Solvolysis of compound 1 above (where $R_1$, $R_2$, $R_3$=H; X=alkyl) in a medium including an organic acid according to the general procedure of DeLuca et al., U.S. Pat. Nos. 4,195,027 and 4,260,549, provides the novel 5,6-cis and 5,6-trans vitamin D-triols, represented by structures 3 and 4 ($R_1$, $R_2$, $R_3$=H) respectively, wherein $R_4$ is an acyl group corresponding to the acyl part of the acid used in the solvolysis medium.

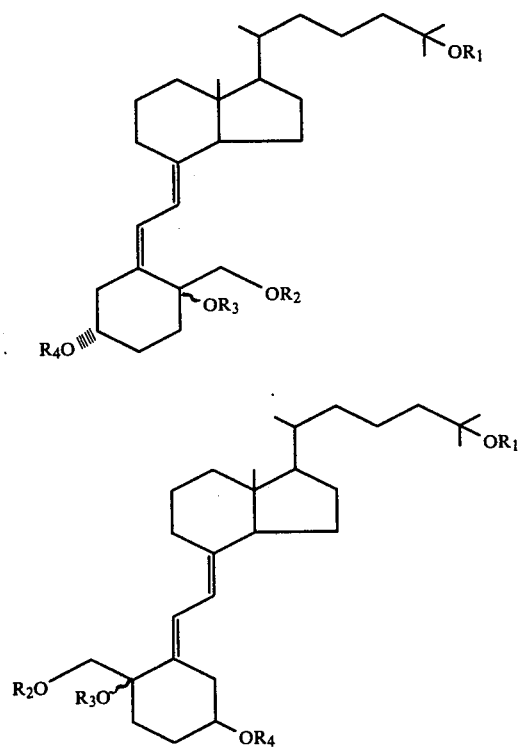

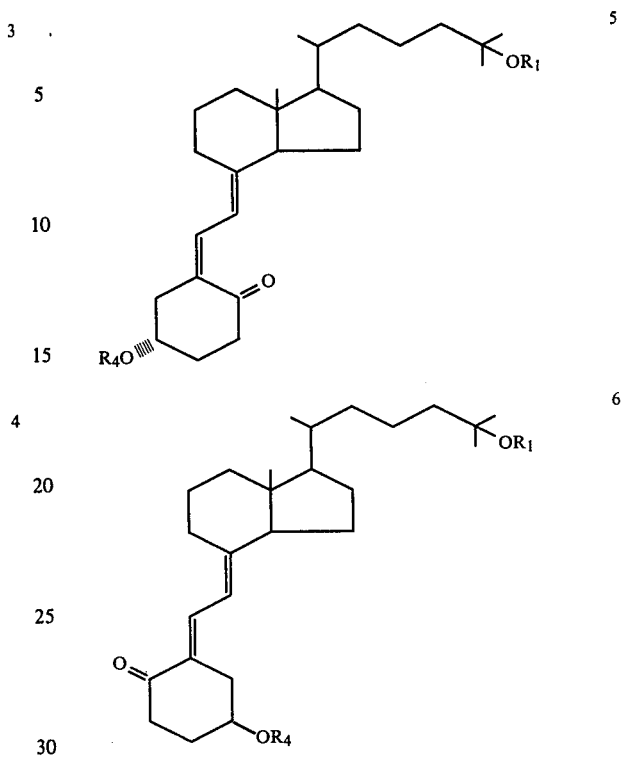

The cis and trans-isomers resulting from solvolysis are conveniently separated (e.g. by chromatography) at this stage and can then be deacylated by conventional base hydrolysis or hydride reduction to the free hydroxy compounds, represented by 3 and 4 above, where $R_1$, $R_2$, $R_3$ and $R_4$ is H. Conventional hydroxy-protecting procedures, i.e. acylation or alkylsilylation, applied to the free hydroxy compounds thus obtained, or to the corresponding 3-0-acyl derivatives, provide, depending on the choice of reagent and conditions, the corresponding partially or completely hydroxy-protected derivatives, i.e. compounds of structure 3 and 4 above, where $R_1$, $R_2$, $R_3$ and $R_4$ is selected from the group consisting of hydrogen, acyl and alkylsilyl.

Cleavage of the vicinal 10,19-diol of compounds 3 or 4 affords the novel 10-oxo-vitamin analogs. Thus, reaction of compound 3 ($R_1$, $R_2$, $R_3$, $R_4$=H) with sodium metaperiodate in a suitable solvent gives the 10-oxo-vitamin analog of structure 5, below ($R_1$, $R_4$=H). Similar treatment of the 5,6-trans-compound 4 ($R_1$, $R_2$, $R_3$, $R_4$=H) provides the corresponding 10-oxo-analog 6 ($R_1$, $R_4$=H). The 3-0-monoacyl derivatives of structure 3 or 4 (as they are obtained from the solvolysis reaction) are equally suitable substrates for the periodate cleavage process, and yield the corresponding 3-0-acyl-10-oxo compounds of structures 5 and 6, respectively, where $R_1$=H and $R_4$=acyl, which are converted to the 3-hydroxy-compounds by standard alkaline hydrolysis, or which, if desired, can be further hydroxy-protected at the C-25-hydroxy position, by conventional methods (e.g. acylation, alkylsilylations).

Alternatively, hydroxy-protected derivatives represented by structure 5 and 6, bearing a hydroxy-protecting group at either C-3 or C-25 or at both positions, are obtained by subjecting the free hydroxy compounds to appropriate hydroxy-protecting procedures, which are well-known in the art.

For example, acetylation of compound 5 ($R_1$, $R_4$=H) with acetic anhydride in pyridine at room temperature gives the 3-monoacetate (5, $R_1$=H, $R_4$=acetyl) whereas the same reaction at elevated temperatures (75°–100°) provides the 3,25-diacetate (5, $R_1$, $R_4$=acetyl). Benzoylation or trimethylsilylation of the 3-monoacetate gives the 3-acetate-25-benzoate (5, $R_1$=benzoyl, $R_4$=acetyl) or the 3-acetate-25-trimethylsilyl derivative ($R_1$=trimethylsily, $R_4$=acetyl) respectively. The 3,25-diacetate is selectively hydrolyzed (e.g. 5% KOH, 10–30 min) to give the 25-monoacetate (5, $R_1$=acetyl, $R_4$=H), and this derivative can be reprotected at C-3 to give the 3,25-di-protected compound, where the protecting group may be the same or different. Exactly analogous procedures, applied to compounds of structure 6 or to the precursor compounds of structure 3 or 4, provide the corresponding partially or fully hydroxy-protected derivatives already mentioned.

The 10-oxo-analogs of this invention, structures 5 and 6 ($R_1$ and $R_4$=H), have been found to be highly effective ligands for binding to the cytosolic intestinal D-receptor protein, and since high affinity for this receptor protein is a characteristic of the biologically potent vitamin D metabolites and analogs [e.g. see DeLuca et al. Topics in Current Chemistry, vol. 83, p. 1 (1979)], the novel compounds of this invention can be expected to have utility as therapeutically effective agents. The 25-hydroxy-substituted cholesterol-side chain in products 5 and 6 is a key structural element accounting for their high receptor-affinity, and it is this feature that distinguishes the compounds of this invention from the 10-oxo-vitamin $D_2$ compounds (5,6-cis and 5,6-trans-10-oxo-19-norvitamin $D_2$) prepared by Harrison and Lythgoe, J. Chem. Soc., p. 837 and 843 (1958).

Throughout the present specification, including the following specific examples, like numbers (e.g. compound 1, 2, 3, etc.) identify like compounds.

EXAMPLE 1

7,8,25-Trihydroxy-7,8-dihydrovitamin $D_3$ 3-acetate (compound 2, $R_1$, $R_2$, $R_3$=H; $R_4$=acetyl)

To a solution of 250 mg of 25-hydroxyvitamin $D_3$ 3-acetate in 2.0 ml of dry pyridine was added 1.67 mL of a 10% solution of $OsO_4$ in pyridine. After 15 min all the starting material had been consumed and 10 mL of 10% $NaHSO_3$ was added. This solution was stirred for 30 min at room temperature, then diluted with 50 mL of 10% $NaHCO_3$ and extracted with ether (3×25 mL). The ether extracts were washed with water (2×25 mL), 1 N HCl (2×25 mL), sat. $NaHCO_3$ (2×25 mL), water (1×50 mL), dried over $Na_2SO_4$ and concentrated to an oil in vacuo. Preparative HPLC (6.2×250 mm Zorbax-Sil column, 15% 2-propanol/hexanes) yielded 185 mg of compound 2 ($R_1$, $R_2$, $R_3$=H; $R_4$=acetyl) as an oil which eluted at 15 mL and possessed the following spectral characteristics: mass spectrum, m/e (relative intensity) 476 ($M^+$, 3), 458 (5), 416 (10), 298 (25), 245 (20), 136 (100), 59 (75); NMR $\delta$ 0.80 (3H, s, 18-$H_3$), 0.92 (3H, d, J=6.0 Hz, 21-$H_3$), 1.23 (6H, s, 26-$H_3$ and 27-$H_3$), 2.04 (3H, s, 3-$OCOCH_3$), 4.81 (1H, m, 3-H), 4.91 (1H, d, J=9.5 Hz, 7-H), 4.95 (1H, s, 19(Z)-H), 5.03 (1H, s, 19(E)-H), 5.58 (1H, d, J=9.5 Hz, 6-H). Alkaline hydrolysis (5% KOH/MeOH, 30 min) of this product provides the corresponding tetrahydroxy-compound, structure 2, $R_1$, $R_2$, $R_3$ and $R_4$=H.

EXAMPLE 2

(6R)-25-Hydroxy-3,5-cyclovitamin $D_3$ 6-methyl ether

A solution of 300 mg of 25-hydroxyvitamin $D_3$ and 350 mg of p-toluenesulfonyl chloride in 2.0 mL of dry pyridine was allowed to react for 48 hr at 5° C. with stirring. The solution was then quenched with sat $NaHCO_3$ and the aqueous phase extracted with ether (3×30 mL). The ether extracts were washed with 1 N HCl (2×20 mL), sat. $NaHCO_3$ (2×30 mL), $H_2O$ (1×50 mL), dried over $MgSO_4$ and concentrated in vacuo. The resulting crude 3$\beta$-tosylate derivative was taken up in 15.0 mL of anhydrous methanol containing 800 mg of $NaHCO_3$ and heated to 55° C. for 6.0 hr. At the end of this period the reaction was cooled, concentrated to 5 mL, diluted with ether and washed with water (3×30 mL). After drying over $MgSO_4$ the ether solution was concentrated to an oil which was shown to be 80% 25-hydroxy-3,5-cyclovitamin $D_3$ by tlc analysis and suitable for subsequent reactions.

EXAMPLE 3

(6R)-10,19-Dihydro-10,19-25-trihydroxy-3,5-cyclovitamin $D_3$ 6-methyl ether (compound 1, $R_1$, $R_2$, $R_3$=H; X=$CH_3$)

To 462 mg of the product of Example 2 in 3.0 mL of dry pyridine was added 3.1 mL of a 10% $OsO_4$ solution in pyridine and the reaction was continued for 10 min, after which it was quenched with 15 mL 10% $NaHSO_3$. After 30 min the reaction was further diluted with 50 ml of $NaHSO_3$ and extracted with ether (3×30 mL). The organic extracts were washed with 1 N HCl (3×40 mL), water (2×40 mL), dried over $MgSO_4$ and concentrated to an oil in vacuo. After HPLC (6.2×250 mm, Zorbax-Sil, 15% 2-propanol/hexanes) compound 1 ($R_2$, $R_2$, $R_3$=H; X=$CH_3$) was obtained in 70% yield as a colorless oil (16 mL elution volume in 70% yield): mass spectrum, m/e (relative intensity), 448 ($M^+$, 3), 430 (5), 416 (45), 398 (15), 367 (40), 269 (40), 245 (35), 59 (100); NMR 0.32 (1H, m, 3-H), 0.52 (2H, m, 4-$H_2$), 0.56 (3H, s, 18-$H_3$), 0.90 (3H, d, J=6.0, 21-$H_3$), 1.23 (6H, s, 26-$H_3$ and 27-$H_3$), 3.25 (3H, s, 6-$OCH_3$), 3.63 (2H, m, 19-$H_2$), 4.60 (1H, d, J=9.2 Hz, 6-H), 4.78 (1H, d, J=9.2 Hz, 7-H).

EXAMPLE 4

(5Z)- and (5E)-10,19,25-Trihydroxy-10,19-dihydrovitamin $D_3$ 3-acetate (compounds 3 and 4, $R_1$, $R_2$, $R_3$=4; $R_4$=acetyl)

A solution of 300 mg of 10,19-diol-cyclovitamin compound 1 ($R_1$, $R_2$, $R_3$=H; X=$CH_3$) in 3.0 mL of glacial acetic acid was heated to 55° C. for 154 min, then quenched by adding dropwise to ice/saturated, $NaHCO_3$. The ether extraction was (3×25 mL) washed with $H_2O$ (2×30 mL), dried over $MgSO_4$ and concentrated in vacuo. The oily crude product, subjected to HPLC purification (6.2×250 mm, Zorbax-Sil, 8% 2-propanol/hexanes), gave the 5,6-cis (5Z)-compound of structure 3 ($R_1$, $R_2$, $R_3$=H; $R_4$=acetyl), eluting at 49 mL, in 48% yield: UV $\lambda_{max}$ 252 nm; mass spectrum, m/e (relative intensity) 476 ($M^+$, 5), 458 (20), 416 (35), 398 (25), 245 (30), 185 (60), 134 (100), 59 (60); NMR $\delta$ 0.55 (3H, s, 18-$H_3$), 0.96 (3H, d, J=6.0 Hz, 21-$H_3$), 1.23 (6H, s, 26-$H_3$ and 27-$H_3$), 2.05 (3H, s, 3-$OCOCH_3$), 3.72 (2H, m, 19-$H_2$), 4.74 (1H, m, 3-H), 5.82 (1H, d, J=11.2 Hz, 7-H), 6.63 (1H, d, J=11.2 Hz, 6-H), and the 5,6-trans (5E)-isomer 4 ($R_1$, $R_2$, $R_3$=H; $R_4$=acetyl), eluting at 27 mL, in 18% yield: UV $\delta_{max}$=250 nm; mass spectrum, m/e (relative intensity) 476 ($M^+$, 2) 458 (6), 416 (30), 398 (30), 245 (25), 185 (40), 134 (100), 59 (80); NMR $\delta$ 0.46 (3H, s, 18-$H_3$), 0.98 (3H, d, J=6.2 Hz, 21-$H_3$), 1.22 (6H, s, 26-$H_3$ and 27-$H_3$), 2.03 (3H, s, 3-$OCOCH_3$), 3.67 (2H, q-AB, J=11.0 Hz, 19-$H_2$), 4.7 (1H, m, 3-H), 6.02 (1H, d, J=15 Hz, 7-H), 6.30 (1H, d, J=15 Hz, 6-H). Mild base hydrolysis of the 3-monoacetates thus obtained gives the corresponding hydroxyvitamin analogs 3 and 4 where $R_1$, $R_2$, $R_3$, and $R_4$=H.

EXAMPLE 5

(5Z)- and (5E)-10-Oxo-25-hydroxy-19-nor-vitamin $D_3$ (compounds 5 and 6, $R_1$, $R_4$=H)

A solution of 50 mg of compound 3 ($R_1$, $R_2$, $R_3$=H; $R_4$=acetyl) in 1.5 m of methanol was treated with 0.5 mL of a saturated solution of $NaIO_4$ in $H_2O$. The reaction was heated to 50° C. for 2.5 hr, diluted with $H_2O$ and extracted with ether (3×30 mL). The ether extracts were washed with $H_2O$ (2×20 mL), dried over $MgSO_4$ and concentrated in vacuo to give compound 5 ($R_1$=H; $R_4$=acetyl). This material was taken up in 3.0 mL of ethanol and treated with 1.0 mL of 5% methanolic NaOH for 30 min at room temperature. The reaction mixture was neutralized with 1 N HCl, concentrated in vacuo and diluted with ether (50 mL). The organic phase was washed with $H_2O$ (2×20 mL), dried over $MgSO_4$ and taken to an oil in vacuo which was purified via HPLC (6.2×250 mm Zorbax-Sil, 14% 2-propanol/hexanes) to give compound 5 ($R_1$, $R_4$=H), eluting at 37 mL, in 72% yield: UV $\lambda_{max}$ 310 nm (=15,000); mass spectrum, m/e (relative intensity) 402 ($M^+$, 35), 384

(30), 369 (10), 359 (45), 341 (15), 273 (35), 177 (50), 135 (70), 133 (100), 59 (60); NMR δ 0.55 (3H, s, 18-H$_3$), 0.96 (3H, d, J=6.0 Hz, 21-H$_3$), 1.22 (6H, s, 26-H$_3$ and 27-H$_3$), 4.2 (1H, M, 3-H), 5.87 (1H, d, J=12.6 Hz, 6-H), 7.61 (1H, d, J=12.6 Hz, 7-H).

Similar treatment of the (5E)-triol 3-acetate (compound 4, R$_1$, R$_2$, R$_3$=H; R$_4$=acetyl) afforded first the 10-oxo-3-acetate compound 6 (R$_1$=H; R$_4$=acetyl) and, after hydrolysis, the 5(E)-10-oxo analog 6 (R$_1$, R$_4$=H) which on HPLC eluted at 34 mL in 14% 2-propanol/hexane and exhibited the following physical characteristics: UV λ$_{max}$ 307 (=24,000); mass spectrum, m/e (relative intensity) 402 (M+, 30), 384 (30), 369 (20), 359 (40), 273 (40), 177 (60), 135 (40), 133 (100), 59 (40); NMR δ 0.56 (3H, s, 18-H$_3$) 0.95 (3H, d, J=6.0 Hz, 21-H$_3$), 1.23 (6H, s, 26-H$_3$ and 27-H$_3$), 4.2 (1H, m, 3-H), 6.65 (2H, q-AB, J=11.8 Hz, 6-H and 7-H).

We claim:

1. A compound having the formula

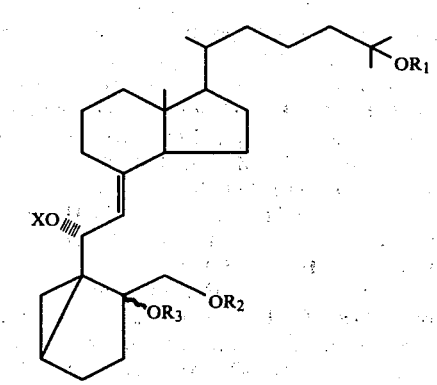

where R$_1$, R$_2$ and R$_3$, which may be the same or different, represent hydrogen or a hydroxy-protecting group, and where X is alkyl.

2. The compound of claim 1 wherein R$_1$, R$_2$ and R$_3$ are hydrogen, and X is methyl.

3. A compound having the formula

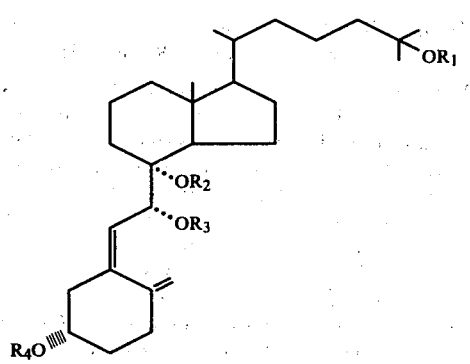

wherein R$_1$, R$_2$, R$_3$ and R$_4$, which may be the same or different represent hydrogen, or a hydroxy-protecting group.

4. A compound selected from the group consisting of

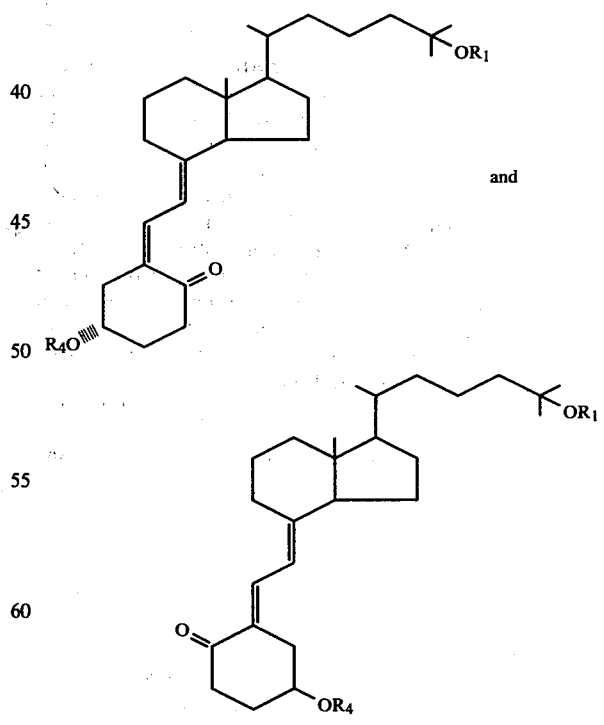

wherein R$_1$, R$_2$, R$_3$ and R$_4$, which may be the same or different, represent hydrogen or a hydroxy-protecting group.

5. A compound according to claim 4, wherein R$_1$, R$_2$, R$_3$ and R$_4$ represent hydrogen.

6. A compound according to claim 4, wherein R$_1$, R$_2$ and R$_3$ represent hydrogen, and R$_4$ is acyl.

7. A compound selected from the group consisting of wherein R$_1$ and R$_4$, which may be the same or different represent hydrogen or a hydroxy-protecting group.

8. 25-Hydroxy-10-oxo-19-norvitamin D$_3$.

9. 25-Hydroxy-10-oxo-19-nor-5,6-trans-vitamin D$_3$.

UNITED STATES PATENT OFFICE
CERTIFICATE OF CORRECTION

Patent No. 4,448,726　　　　　　　　Dated　May 15, 1984

Inventor(s) Hector F. DeLuca et al

It is certified that error appears in the above-identified patent and that said Letters Patent are hereby corrected as shown below:

In Column 1, before the first paragraph insert -- This invention was made with Government support under NIH Grant No. AM-14881 awarded by the Department of Health and Human Services. The Government has certain rights in this invention. --

Signed and Sealed this

Twenty-third Day of October 1984

[SEAL]

*Attest:*

*Attesting Officer*

GERALD J. MOSSINGHOFF

*Commissioner of Patents and Trademarks*